US00PP11583P

United States Patent [19]

Meilland

[11] Patent Number: Plant 11,583

[45] Date of Patent: Oct. 17, 2000

[54] GROUND COVER ROSE PLANT NAMED 'MEIPSIDUE'

[75] Inventor: Alain A. Meilland, Antibes, France

[73] Assignee: CP (Delaware), Inc., Wilmington, Del.

[21] Appl. No.: 09/150,065

[22] Filed: Sep. 9, 1998

[51] Int. Cl.[7] ..... A01H 5/00

[52] U.S. Cl. ..... Plt./108

[58] Field of Search ..... Plt./101, 102, 108, Plt./122, 116

*Primary Examiner*—Howard J. Locker

*Attorney, Agent, or Firm*—Burns, Doane, Swecker & Mathis, L.L.P.

[57] ABSTRACT

A new and distinct variety of ground cover rose plant (i.e., garden rose plant) is provided which forms in abundance on a substantially continuous basis attractive double blossoms that are Rose Bengal suffused with Cardinal Red. The overall coloration of the blossoms is velvet red. The vegetation is vigorous and the growth habit is flat and bushy. Attractive decorative medium green and glossy foliage is formed. Excellent disease resistance is exhibited. Additionally, the new variety grows very well on its own roots following asexual reproduction by cuttings.

4 Drawing Sheets

SUMMARY OF THE INVENTION

The new variety of ground cover *Rosa hybrida* rose plant of the present invention was created by artificial pollination wherein two parents were crossed which previously had been studied in the hope that they would contribute the desired characteristics. The female parent (i.e., the seed parent) of the new variety was the product of the cross between the 'Kormax' variety (non-patented in the United States) and the 'Meibeluxen' variety (non-patented in the United States). The male parent (i.e., the pollen parent) of the new variety was the 'Meineble' variety (U.S. Plant Pat. No. 7,116). The parentage of the new variety can be summarized as follows:

('Kormax'×'Meibeluxen')×'Meineble'.

The seeds resulting from the above pollination were sown and small plants were obtained which were physically and biologically different from each other. Selective study resulted in the identification of a single plant of the new variety.

It was found that the new variety of ground cover rose plant of the present invention possesses the following combination of characteristics:

(a) Abundantly and substantially continuously forms attractive double blossoms that are Rose Bengal suffused with Cardinal Red,
(b) Exhibits a flat and bushy growth habit,
(c) Forms vigorous vegetation,
(d) Forms attractive decorative medium green and glossy foliage,
(e) Propagates well by cuttings, and
(f) Exhibits excellent disease resistance with respect to blackspot, downy mildew and powdery mildew.

The new variety reblooms in abundance.

The new variety of the present invention can be readily distinguished from its parent varieties. For instance, the 'Kormax' variety forms a red single flower. The 'Meibeluxen' variety forms a semi-double red flower, and the 'Meineble' variety forms a red single flower with a white eye.

The new variety well meets the needs of the horticultural industry. It can be grown to advantage as an attractive ornamentation in parks, gardens, public areas, and residential landscapes. Accordingly, it is particularly well suited for growing in the landscape.

The characteristics of the new variety have been found to be homogeneous and stable and are strictly transmissible by asexual propagation at Le Cannet-des-Maures, Var France such as budding, grafting, and cuttage from one generation to another. The plant propagates well and grows very well on its own roots.

The new variety has been named the 'Meipsidue' variety.

BRIEF DESCRIPTION OF THE PHOTOGRAPHS

The accompanying photographs show, as nearly true as it is reasonably possible to make the same in color illustrations of this character, typical specimens of the plant and plant parts of the new variety. The rose plants of the new variety illustrated herein were three years of age and were grown outdoors during October on their own roots at LeCannet-des-Maures, Var, France.

DETAILED DESCRIPTION

Figure 1:
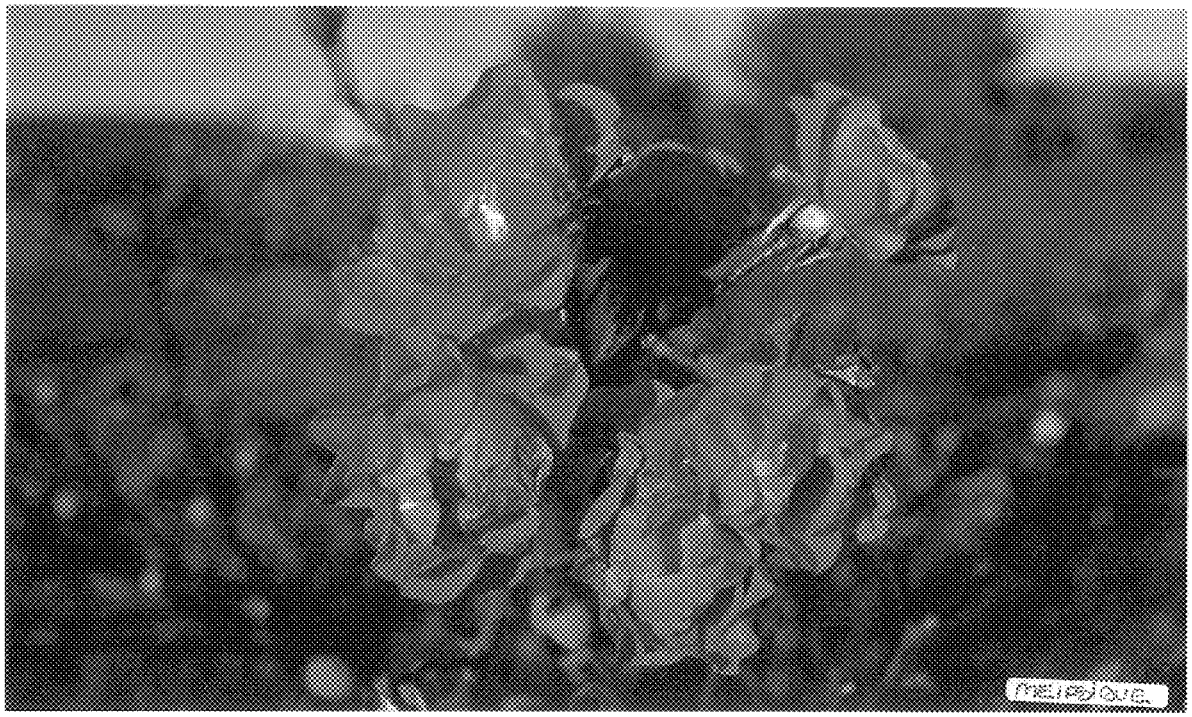
FIG. 1 illustrates typical blossoms of the new variety. The attractive velvet red blossoms are shown.
Figure 2:
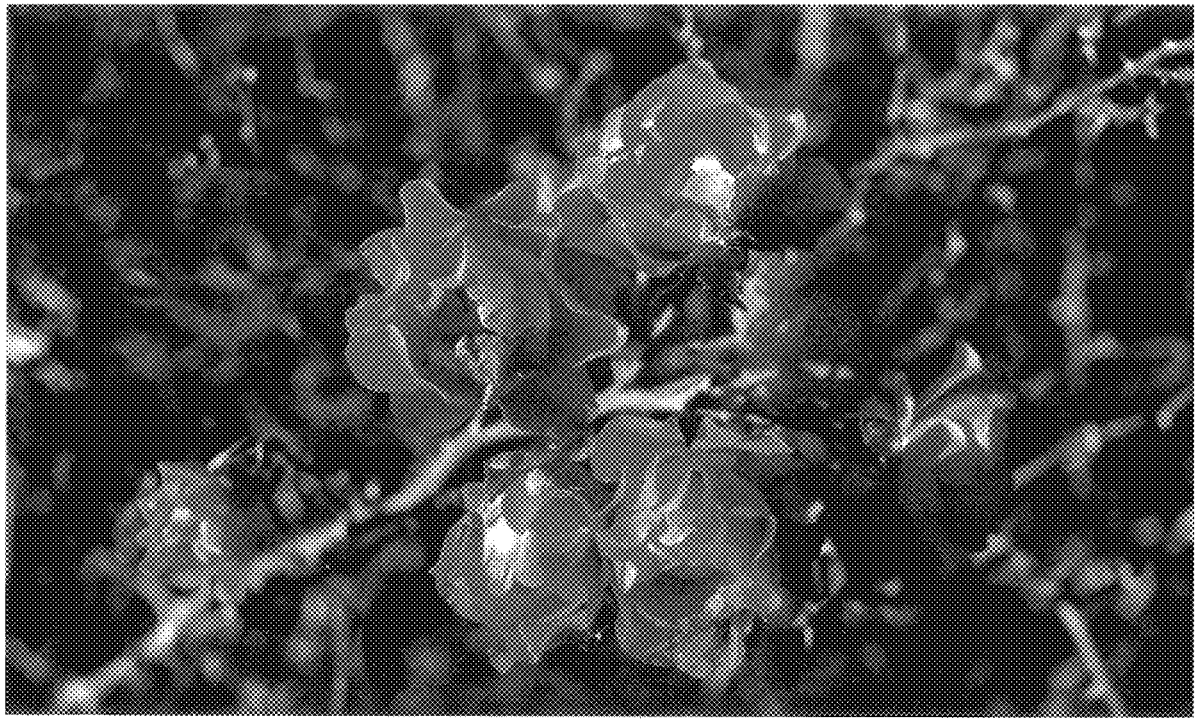
FIG. 2 illustrates a further view of typical blossoms and stems of the new variety.
Figure 3:
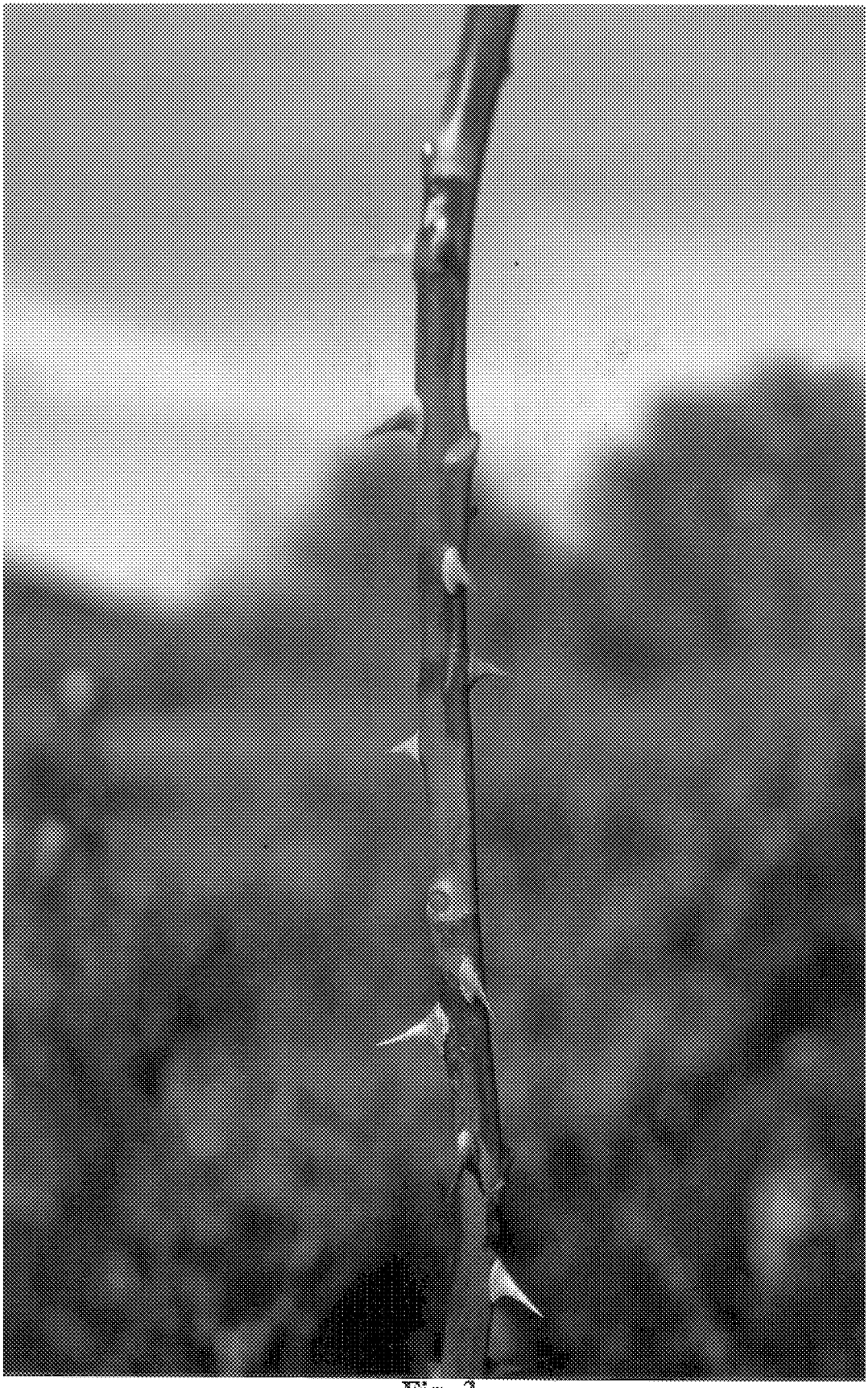
FIG. 3 illustrates a typical cane of the new variety wherein thorns and buds are shown.

The chart used in the identification of colors is that of The Royal Horticultural Society (R.H.S. Colour Chart). The terminology which precedes reference to the chart has been added to indicate the corresponding color in more common terms. The description is based on one-year-old specimens of the new variety during December and grown on their own roots outdoors at LeCannet-des-Maures, Var, France.

Class: Ground cover (garden rose).

Plant:

*Height*.—Approximately 40 cm. on average at the end of the growing season.

*Width*.—Approximately 100 cm. on average at the end of the growing season.

*Habit*.—Flat and bushy.

Branches:

*Color*.—Young stems: Light green, near Yellow-Green Group 146C. Adult wood: Light green, near Yellow-Green Group 146B.

*Thorns*.—Size: Medium (as illustrated). Quantity: Medium (as illustrated). Color: Reddish on young stems and with some change to tan (Greyed-Orange Group 177C) when mature on adult wood.

Leaves:

*Stipules*.—Adnate, pectinate, and rather large.

*Petioles*.—Upper surface: With a few glands on the edges. Under surface: Bear some prickles.

*Leaflets*.—Number: 3, 5 (most often), and 7. Size: Medium. Shape: Oval with undulated margins. Texture: Consistent. Overall appearance: Very dense, medium green in coloration, and glossy. Color (young foliage): Upper surface: Medium green, Yellow-Green Group 146A. Under surface: Lighter green, near Yellow-Green Group 146B. Color (adult foliage): Upper surface: Medium green, near Yellow-Green Group 146A. Under surface: Lighter green, near Yellow-Green Group 146B.

Inflorescence:

*Number of flowers*.—Commonly approximately 6 to 15 blooms per floral stem.

*Peduncle*.—Medium in size and rigid with some aciculae, reddish when young, and approximately 2 cm. in length on average.

*Sepals*.—Upper surface: Greenish in coloration. Under surface: Light green in coloration.

*Buds*.—Shape: Conical. Length: Approximately 1.5 cm. on average. Size: Small. Color (when opening): Upper surface: Near Crimson Red, Red Group 52A, and widely suffused with near Cardinal Red, Red Group 53A. Under surface: Near Cardinal Red, Red Group 53B.

*Flower*.—Form: Cup-shaped, and double. Diameter: Approximately 5 to 6 cm. on average. Color (when opening begins): Upper surface: Near Rose Bengal, Red-Purple Group 57B and very widely suffused with near Cardinal Red, Red Group 53A. Under surface: Near Cardinal Red, Red Group 53C. Color (when blooming): Upper surface: Near Rose Bengal, Red-Purple Group 57B and very widely suffused with near Cardinal Red, Red Group 53A. Under surface: Near Cardinal Red, Red Group 53C. Color (at end of blooming): Upper surface: Near Red-Purple Group 61B and very widely suffused with near Cardinal Red, Red Group 53A. Under surface: Near Red-Purple Group 61B. Fragrance: None. Lasting quality: The blossoms commonly last approximately 5 to 7 days on the plant and when cut and placed in a vase. Petal form: Rounded. Petal number: Approximately 30 on average. Stamen number: Approximately 84 on average. Anthers: Orange yellow in coloration. Filaments: Yellow in coloration. Pollen: Orange-yellow in coloration. Pistils: Approximately 32 on average. Stigmas: White in coloration. Styles: Greenish in coloration. Receptacle: Light green in coloration, and in longitudinal section it is in the shape of a pear. Hips: Approximately 1.5 cm in size, the coloration commonly is variable from Greyed-Orange Group 173A and 173B to Greyed-Purple Group 183B. Commonly approximately 3 to 6 fertile seeds are present.

Development:

*Vegetation*.—Strong.

*Blossoming*.—Very abundant and substantially continuous.

Figure 4:
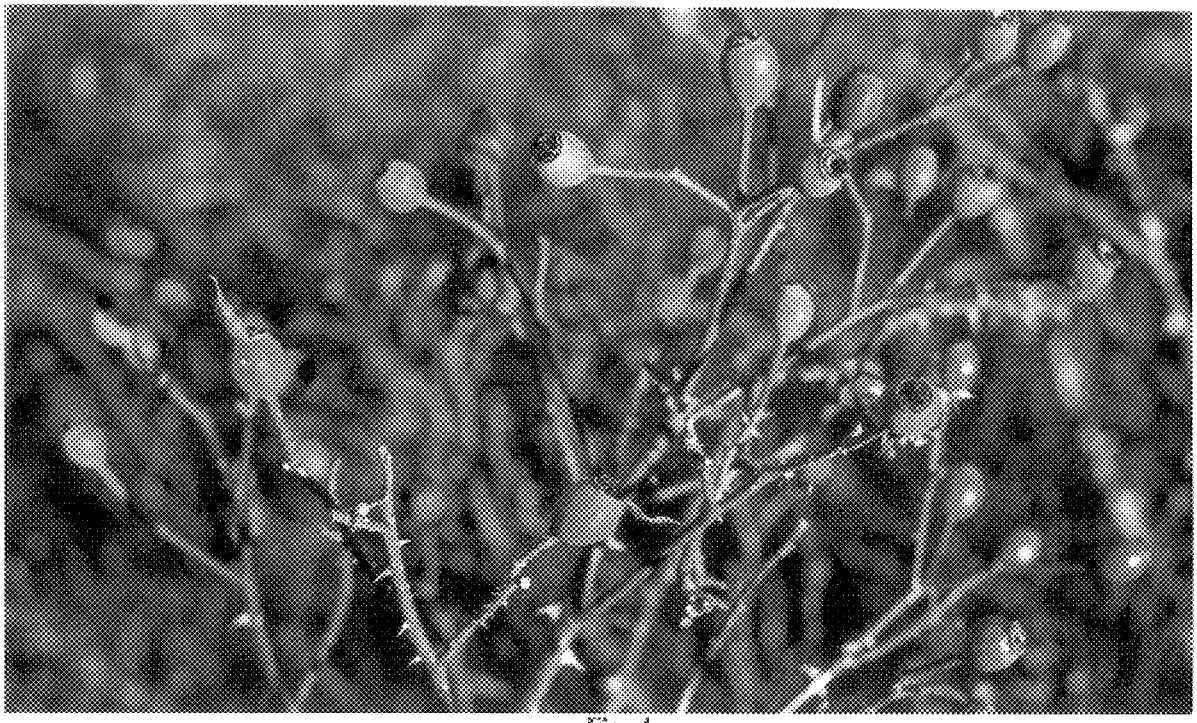
FIG. 4 illustrates typical hips that are formed in abundance on the new variety.

*Aptitude to bear fruits*.—Very good, as illustrated in FIG. 4.

*Resistance to diseases*.—Excellent with respect to blackspot, downy mildew, and powdery mildew.

*Hardiness*.—Has well withstood temperatures of −10° F. in U.S.D.A. Hardiness Zone No. 5.

I claim:

1. A new and distinct variety of ground cover rose plant characterized by the following combination of characteristics:

(a) abundantly and substantially continously forms attractive double blossoms that are Rose Bengal suffused with Cardinal Red,
(b) exhibits a flat and bushy growth habit,
(c) forms vigorous vegetation,
(d) forms attractive decorative medium green and glossy foliage,
(e) propagates well by cuttings, and
(f) exhibits excellent disease resistance with respect to blackspot, downy mildew, and powdery mildew;

substantially as herein shown and described.

* * * * *